(12) United States Patent
Bucala et al.

(10) Patent No.: US 9,221,903 B2
(45) Date of Patent: Dec. 29, 2015

(54) METHOD OF INHIBITING BINDING OR ACTIVITY OF MIF BY ADMINISTERING A MIF ANTAGONIST

(71) Applicants: Baxter International Inc., Deerfield, IL (US); Baxter Healthcare SA, Glattpark (Opfikon) (CH)

(72) Inventors: Richard J. Bucala, Cos Cob, CT (US); Lin Leng, New York, NY (US); Christine N. Metz, Great Neck, NY (US)

(73) Assignees: Baxalta Incorporated, Bannockburn, IL (US); Baxalta GmbH, Glattpark (Opfikon) (CH)

( * ) Notice: Subject to any disclaimer, the term of this patent is extended or adjusted under 35 U.S.C. 154(b) by 0 days.

(21) Appl. No.: 14/090,183

(22) Filed: Nov. 26, 2013

(65) Prior Publication Data

US 2014/0178403 A1    Jun. 26, 2014

Related U.S. Application Data (60) Continuation of application No. 12/781,546, filed on May 17, 2010, now Pat. No. 8,617,822, which is a division of application No. 11/931,442, filed on Oct. 31, 2007, now Pat. No. 7,741,057, which is a continuation of application No. 10/108,383, filed on Mar. 29, 2002, now abandoned.

(60) Provisional application No. 60/279,435, filed on Mar. 29, 2001.

(51) Int. Cl.

| A61K 38/16 | (2006.01) |
| --- | --- |
| A61K 38/17 | (2006.01) |
| A61K 38/19 | (2006.01) |
| A61K 35/00 | (2006.01) |
| C07K 16/24 | (2006.01) |
| G01N 33/50 | (2006.01) |
| G01N 33/68 | (2006.01) |
| C07K 16/28 | (2006.01) |
| C07K 16/40 | (2006.01) |
| C12N 9/90 | (2006.01) |
| C12N 15/113 | (2010.01) |
| C07K 14/47 | (2006.01) |
| C07K 14/52 | (2006.01) |
| A61K 39/00 | (2006.01) |

(52) U.S. Cl.
CPC .......... *C07K 16/24* (2013.01); *A61K 38/17* (2013.01); *C07K 16/2833* (2013.01); *C07K 16/40* (2013.01); *C12N 9/90* (2013.01); *C12N 15/1138* (2013.01); *G01N 33/5047* (2013.01); *G01N 33/6863* (2013.01); *A61K 38/1709* (2013.01); *A61K 38/19* (2013.01); *A61K 2039/505* (2013.01); *C07K 14/47* (2013.01); *C07K 14/52* (2013.01); *C12Y 503/02001* (2013.01); *C12Y 503/03012* (2013.01); *G01N 2333/52* (2013.01); *G01N 2333/99* (2013.01); *G01N 2500/02* (2013.01)

(58) Field of Classification Search
None
See application file for complete search history.

(56) References Cited

U.S. PATENT DOCUMENTS

| 5,559,028 A | 9/1996 | Humphreys |
| 5,726,020 A | 3/1998 | Humphreys et al. |
| 6,030,615 A | 2/2000 | Bucala et al. |
| 6,080,407 A | 6/2000 | Bucala et al. |
| 6,395,276 B1 | 5/2002 | Rybak et al. |
| 6,492,428 B1 | 12/2002 | Al-Abed et al. |
| 6,599,938 B1 | 7/2003 | Al-Abed et al. |
| 6,774,227 B1 | 8/2004 | Bucala et al. |
| 7,514,225 B2 | 4/2009 | Gaeta et al. |
| 8,617,822 B2 * | 12/2013 | Bucala et al. .............. 435/7.1 |

FOREIGN PATENT DOCUMENTS

| CA | 2205680 | 11/1998 |
| WO | WO 97/25344 A1 | 7/1997 |
| WO | WO 97/29635 A1 | 8/1997 |
| WO | WO-9817314 A1 * | 4/1998 |
| WO | WO 98/37178 A1 | 8/1998 |
| WO | WO 01/32606 A1 | 5/2001 |

OTHER PUBLICATIONS

"COS-7" cell line database from invitrogen, www.invitrogen.com/site/us/en/home/support/Cell-Lines-Browse/Cell-LinesResults/Cell-Lines-Detail.5.html; downloaded May 19, 2012; 2 total pages.*
"COS-7" datasheet from ATCC, www.atcc.org/attachments/17445.pdf; downloaded May 19, 2012; 3 total pages.*
"Raji" cell line database from invitrogen, www.invitrogen.com/site/us/en/home/support/Cell-Lines-Browse/Cell-LinesResults/Cell-Lines-Detail.27.html; downloaded May 19, 2012; 1 page.*
"Raji" datasheet from ATCC, www.atcc.org/attachments/17457.pdf; downloaded May 19, 2012; 3 total pages.*
Chesney et al. An essential role for macrophage inhibitory factor (MIF) in angiogenesis and the growth of a murine lymphoma. Mol Med 5: 181-191, 1999.*
Das, U.N. Critical advances in septicemia and septic shock. Crit Care 4: 290-296, 2000.*
Morand et al. Macrophage inhibitory factor in rheumatoid arthritis: clinical correlations. Rheumatology 41: 558-562, 2002.*

(Continued)

*Primary Examiner* — Bridget E Bunner
(74) *Attorney, Agent, or Firm* — Morgan, Lewis & Bockius LLP (57) ABSTRACT

Methods and compositions for using the MHC class II invariant chain polypeptide, Ii (also known as CD74), as a receptor for macrophage migration inhibitory factor (MIF), are disclosed. These include methods and compositions for using this receptor, as well as agonists and antagonists of MIF which bind to this receptor, or which otherwise modulate the interaction of MIF with CD74 or the consequences of such interaction, in treatment of conditions characterized by locally or systemically altered MIF levels, particularly inflammatory conditions and cancer.

8 Claims, 8 Drawing Sheets

(56) References Cited

OTHER PUBLICATIONS

Horton et al. Potent in vitro and in vivo activity of an Fc-engineered anti-CD19 monoclonal antibody against lymphoma and leukemia. Cancer Res 68(19): 8049-8057, 2008.*

Epstein et al. Characteristics and mode of growth of a tissue culture strain (EB1) of human lymphoblasts from Burkitt's lymphoma. J Natl Cancer Institute 34(2): 231-240, 1965.*

Pulvertaft et al. Cytology of Burkitt's tumour (African lymphoma). The Lancet 1(7327): 238-240, 1964.*

Mao et al. Milatuzumab-conjugated liposomes as targeted dexamethasone carriers for therapeutic delivery in CD74+ B-cell malignancies. Clin Cancer Res 19(2): 347-356, 2013.*

Bernhagen et al. The emerging role of MIF in septic shock and infection. Biotherapy 8: 123-127, 1995.*

Ashman, Jonathan B. et al., "A Role for the Transmembrane Domain in the Trirnerization of the MHC Class II-associated Invariant Chain", J. Immunol., vol. 163, pp. 2704-2712 (1999).

Bacher, Michael et al., "An essential regulatory role for macrophage migration inhibitory factor in T-cell activation", Proc. Natl. Acad. Sci. USA, vol. 93, pp. 7849-7854 (1996).

BD Pharmingen technical data sheet for CD74 for purified mouse anti-human CD74 monoclonal antibody (clone M-B741), 2007.

BD Pharmingen technical data sheet for purified mouse anti-human CD74 monoclonal antibody (clone LN2), 2007.

Bendrat, Klaus et al., "Biochemical and Mutational Investigations of the Enzymatic Activity of Macrophage Migration Inhibitory Factor (MIF)", Biochemistry, vol. 36, pp. 15356-15362 (1997).

Bernhagen, Jurgen et al, "An essential role for macrophage migration inhibitory factor (MIF) in the tuberculin delayed-type hypersensitivity reaction", J. Exp. Med., vol. 183, pp. 277-282 (1996).

Bozza, Marcelo et al., "Targeted Disruption of Migration Inhibitory Factor Gene Reveals its Critical Role in Sepsis", J. Exp. Med., vol. 189, No. 2, pp. 341-346 (1999).

Calandra, Thierry et al., "MIF as a glucocorticoid-induced modulator of cytokine production", Nature, vol. 377, pp. 68-71 (1995).

Calandra, Thierry et al., "Protection from septic shock by neutralization of macrophage migration inhibitory factor", Nature Med., vol. 6, No. 2, pp. 164-170, (2000).

Calandra, Thierry et al., "The Macrophage Is an Important and Previously Unrecognized Source of Macrophage Migration Inhibitory Factor", J. Exp. Med., vol. 179, pp. 1895-1902 (1994).

Carter, P. Bispecific human IgG by design. J Immunol Meth 248: 7-15, 2001.

Co et al. Chimeric and humanized antibodies with specificity for the CD33 antigen. J Immunol 148(4): 1149-1154, 1992.

Cournia, Z. et al., "Discovery of Human Macrophage Migration Inhibitory Factor (MIF)-CD74 Antagonists via Virtual Screening," J. Med. Chem., Jan. 22, 2009, vol. 52, No. 2, pp. 416-424.

Cresswell, Peter, "Assembly, Transport, and Function of MHC Class II Molecule", Annu. Rev. Immunol., vol. 12, pp. 259-293 (1994).

D'Andrea, Alan D. et al., "Expression Cloning of the Murine Erythropoietin Receptor", Cell, vol. 57, pp. 277-285, (1989).

Denzin, Lisa K. et al., "HLA-DM Induces CLIP Dissociation from MHC Class 11 αβ Dimers and Facilitates Peptide Loading", Cell, vol. 82, Jul. 14, 1995, pp. 155-165.

Gore,Y. et al., "Macrophage Migration Inhibitory Factor Induces B Cell Survival by Activation of a CD74-CD44 Receptor Complex," *The Journal of Biological Chemistry*, Feb. 1, 2008, vol. 283, No. 5, pp. 2784-2792.

Gray et al. Therapeutic potential of immunostimulatory monoclonal antibodies. Clin Sci 111: 96-106, 2006.

Hansen, Hans J. et al., "Internalization and catabolism of radiolabelled antibodies to MHC class-II invariant chain by B-cell lymphomas", Biochem. J., vol. 320, pp. 293-300 (1996).

Hudson, James D. et al., "A Proinflammatory Cytokine Inhibits p53 Tumor Suppressor Activity", J. Exp. Med., vol. 190, No. 10, pp. 1375-1382 (1999).

Ioachim et al., Am J. Surg. Pathol. 1996 20(1):64-71.

Kleemann, Robert et al., "Intracellular action of the cytokine MIF to modulate AP-1 activity and the cell cycle through Jab1", Nature, vol. 408, pp. 211-216 (2000).

Koch, Norbert et al., "Differential Expression of the Invariant Chain in Mouse Tumor Cells: Relationship to B Lymphoid Development", Immunol., vol. 132, No. 1, pp. 12-15 (1984).

Kortt et al. Dimeric and trimeric antibodies: high avidity scFvs for cancer targeting. Biomolec Engin 18: 95-108, 2001.

Lan, Hui Y. et al., "The Pathogenic Role of Macrophage Migration Inhibitory Factor (MIF) in Immunologically Induced Kidney Disease in the Rat", J. Exp. Med., vol. 185, No. 8, pp. 1455-1465 (1997).

Lazova, Rossitza et al., "A Marker to Distinguish Atypical Fibroxanthoma from Malignant Fibrous Histiocytoma", American Cancer Society, vol. 79, No. 11, pp. 2115-2124 (1997).

Leng, L. et al., "MIF Signal Transduction Initiated by Binding to CD74," J. Exp. Med., Jun. 2, 2003, vol. 197, No. 11, pp. 1467-1476.

Lesley, Jayne et al., "CD44 and its Interaction with Extracellular Matrix", Adv. In Immunol., vol. 54, pp. 271-335 (1993).

Metz, Christine et al., "A compendium of cytokines and other mediators of host defense" Ligands Review: MIF, eds. Oppenheim, et al., Academic Press, San Diego, pp. 703-716 (2000).

Meyer-Siegler, K.L. et al., "Inhibition of Macrophage Migration Inhibitory Factor or Its Receptor (CD74) Attenuates Growth and Invasion of DU-145 Prostate Cancer Cells," The Journal of Immunology, 2006, vol. 177, pp. 8730-8739.

Mikulowska, Anna et al., "Macrophage Migration Inhibitory Factor (MIF) Is Involved in the Pathogenesis of Collagen Type II-induced Arthritis in Mice", J. Immunol., vol. 158, 5514-5517 (1997).

Mitchell, Robert A. et al., "Sustained Mitogen-activated Protein Kinase (MAPK) and Cytoplasmic Phospholipase A2 Activation by Macrophage Migration Inhibitory Factor (MT)", J. Biol. Chem., vol. 274, No. 25, pp. 18100-18106 (1999).

Naujokas, Marisa et al., "Potent Effects of Low Levels of MHC Class II associated Invariant Chain on CD4., T Cell Development", Immunity, vol. 3, pp. 359-372 (1995).

Naujokas, Marisa et al., "The Chondroitin Sulfate Form of Invariant Chain Can Enhance Stimulation of T Cell Responses Through Interaction with CD44", Cell, vol. 74, pp. 257-268 (1993).

Ngo, J.T. et al., "Computational Complexity, Protein Structure Prediction, and the Levinthal Paradox," The Protein Folding Problem and Teritaty Structure Predictors, 1994, pp. 492-495.

Palupi, et al., "Bovine (3-lactoglobulin receptors on transformed mammalian cells (hybridomas MARK-3): characterization by flow cytometry", J. Biotech., vol. 78, pp. 171-184.

Panchuk-Voloshina, Nataliya et al., "Alexa Dyes, a Series of New Fluorescent Dyes That Yield Exceptionally Bright, Photostable Conjugates", J. Histochem. Cytochem., vol. 47, No. 9, pp. 1179-1188 (1999).

Quaranta, Vito et at., "A Human Ia Cytoplasmic Determinant Located on Multiple Forms of Invariant Chain (γ, γ2, γ3)1", The Journal of Immunology, vol. 132, No. 4, Apr. 1984.

Sant, Andrea J. et al., "Biosynthetic Relationships of the Chondroitin Sulfate Proteoglycan with Ia and Invariant Chain Glycoproteins", J. Immunol., vol. 135, No. 1, pp. 416-422 (1985).

Schlossman, S.F. et al., Leucocyte Typing V on CD-ROM, White Cell Differentiation Antigens, 1996 Oxford University Press.

Shachar, I. et al., "The secret second life of an innocent chaperone: the story of CD74 and B cell/chronic lymphocytic leukemia cell survival," Leukemia & Lymphoma, Aug. 2011, vol. 52, No. 8, pp. 1446-1454.

Shachar, Idit et al., "Requirement for Invariant Chain in B Cell Maturation and Function", Science, vol. 274, pp. 106-108 (1996).

Strubin, Michel et al., "Two Forms of the Ia Antigen-Associated Invariant Chain Result from Alternative Initiations at Two In-Phase AUGs", Cell, vol. 47, pp. 619-625 (1986).

Swope, M.D. et al., "Macrophage Migration Inhibitory Factor: Cytokine, Hormone, or Enzyme?", Rev. Physiol. Biochem. Pharmacol., vol. 139, pp. 1-32 (1999).

Thurman, Gary B. et al., "MIF-like Activity of Natural and Recombinant Human Interferon-y and Their Neutralization by Monoclonal Antibody", J. Immunol., vol. 134, No. 1, pp. 305-309 (1985).

Vaughan et al., Nature Biotechnology, 1998, 535-539.

(56) References Cited

OTHER PUBLICATIONS

Vidal, L. et al., "Making sense of antisense," *European Journal of Cancer*, 2005, vol. 41, pp. 2812-2818.

Wang, Xiao-Fan et al., "Expression Cloning and Characterization of the TGF-β Type III Receptor", Cell, vol. 67, pp. 797-805 (1991).

Weiser, Weishui et al., "Molecular cloning of a cDNA encoding a human macrophage migration inhibitory factor", Proc. Natl. Acad. Sci. USA, vol. 86, pp.' 7522-7526 (1989).

Wells, J.A., "Additivity of Mutational Effects in Proteins," *Biochemistry*, Sep. 18, 1990, vol. 29, No. 37, pp. 8509-8517.

Wraight, Christopher J. et al., "Human Major Histocompatibility Complex Class 11 Invariant Chain Is Expressed on the Cell Surface", The Journal of Biological Chemistry, vol. 265, No. 10, Apr. 5, 1990, pp. 5787-5792.

Wymann, D. et al., "Human B cells secrete migration inhibition factor (MT) and present a naturally processed MIF peptide on HLA-DRBl*0405 by a FXXL motif", Immunology, vol. 96.

Yamasaki, Katsuhiko et al., "Cloning and Expression of the Human Interleukin-6 (BSF-2/IFNβ2) Receptor", Science, vol. 241, pp. 825-828 (1988).

\* cited by examiner

Legend:
—— -CDS ▬ ▬ other feature

Sequence:

| | | | | | | | | |
|---|---|---|---|---|---|---|---|---|
| 1 | TTCCCAGATG | CACAGGAGGA | GAAGCAGGAG | CTGTCGGGAA | GATCAGAAGC | CAGTCATGGA | | putative p33 |
| | M | H R R | R S R S | C R E | D Q K | P V M D | | putative p33 |
| | | | | | | M D | | |
| 61 | TGACCAGCGC | GACCTTATCT | CCAACAATGA | GCAACTGCCC | ATGCTGGGCC | GGCGCCCTGG | | putative p33 |
| | D Q R | D L I | S N N E | Q L P | M L G | R R P G | | putative p33 |
| | D Q R | D L I | S N N E | Q L P | M L G | R R P G | | |
| 121 | GGCCCCGGAG | AGCAAGTGCA | GCCGCGGAGC | CCTGTACACA | GGCTTTTCCA | TCCTGGTGAC | | putative p33 |
| | A P E | S K C | S R G A | L Y T | G F S | I L V T | | putative p33 |
| | A P E | S K C | S R G A | L Y T | G F S | I L V T | | |
| 181 | TCTGCTCCTC | GCTGGCCAGG | CCACCACCGC | CTACTTCCTG | TACCAGCAGC | AGGGCCGGCT | | putative p33 |
| | L L L | A G Q | A T T A | Y F L | Y Q Q | Q G R L | | putative p33 |
| | L L L | A G Q | A T T A | Y F L | Y Q Q | Q G R L | | |
| 241 | GGACAAACTG | ACAGTCACCT | CCCAGAACCT | GCAGCTGGAG | AACCTGCGCA | TGAAGCTTCC | | putative p33 |
| | D K L | T V T | S Q N L | Q L E | N L R | M K L P | | putative p33 |
| | D K L | T V T | S Q N L | Q L E | N L R | M K L P | | |
| 301 | CAAGCCTCCC | AAGCCTGTGA | GCAAGATGCG | CATGGCCACC | CCGCTGCTGA | TGCAGGCGCT | | putative p33 |
| | K P P | K P V | S K M R | M A T | P L L | M Q A L | | putative p33 |
| | K P P | K P V | S K M R | M A T | P L L | M Q A L | | |
| 361 | GCCCATGGGA | GCCCTGCCCC | AGGGGCCCAT | GCAGAATGCC | ACCAAGTATG | GCAACATGAC | | putative p33 |
| | P M G | A L P | Q G P M | Q N A | T K Y | G N M T | | putative p33 |
| | P M G | A L P | Q G P M | Q N A | T K Y | G N M T | | |
| 421 | AGAGGACCAT | GTGATGCACC | TGCTCCAGAA | TGCTGACCCC | CTGAAGGTGT | ACCCGCCACT | | putative p33 |
| | E D H | V M H | L L Q N | A D P | L K V | Y P P L | | putative p33 |
| | E D H | V M H | L L Q N | A D P | L K V | Y P P L | | |
| 481 | GAAGGGGAGC | TTCCCGGAGA | ACCTGAGACA | CCTTAAGAAC | ACCATGGAGA | CCATAGACTG | | putative p33 |
| | K G S | F P E | N L R H | L K N | T M E | T I D W | | putative p33 |
| | K G S | F P E | N L R H | L K N | T M E | T I D W | | |
| 541 | GAAGGTCTTT | GAGAGCTGGA | TGCACCATTG | GCTCCTGTTT | GAAATGAGCA | GGCACTCCTT | | putative p33 |
| | K V F | E S W | M H H W | L L F | E M S | R H S L | | putative p33 |
| | K V F | E S W | M H H W | L L F | E M S | R H S L | | |
| 601 | GGAGCAAAAG | CCCACTGACG | CTCCACCGAA | AGAGTCACTG | GAACTGGAGG | ACCCGTCTTC | | putative p33 |
| | E Q K | P T D | A P P K | E S L | E L E | D P S S | | putative p33 |
| | E Q K | P T D | A P P K | E S L | E L E | D P S S | | |
| 661 | TGGGCTGGGT | GTGACCAAGC | AGGATCTGGG | CCCAGTCCCC | ATGTGAGAGC | AGCAGAGGCG | | |
| | G L G | V T K | Q D L G | P V P | M | | | putative p33 |
| | G L G | V T K | Q D L G | P V P | M | | | putative p33 |
| 721 | GTCTTCAACA | TCCTGCCAGC | CCCACACAGC | TACAGCTTTC | TTGCTCCCTT | CAGCCCCCAG | | |
| 781 | CCCCTCCCCC | ATGTCCCACC | CTGTACCTCA | TCCCATGAGA | CCTGGTGCCT | GGCTCTTTCG | | |
| 841 | TCACCCTTGT | ACAAGACAAA | CCAAGTCGGA | ACAGCAGATA | ACAATGCAGC | AAGGCCCTGC | | |
| 901 | TGCCCAATCT | CCATCTGTCA | ACAGGGGCGT | GAGGTCCCAG | GAAGTGGCCA | AAAGCTAGAC | | |
| 961 | AGATCCCCGT | TCCTGACATC | ACAGCAGCCT | CCAACACAAG | GCTCCAAGAC | CTAGGCTCAT | | |
| 1021 | GGACGAGATG | GGAAGGCACA | GGGAGAAGGG | ATAACCCTAC | ACCCAGACCC | CAGGCTGGAC | | |
| 1081 | ATGCTGACTG | TCCTCTCCCC | TCCAGCCTTT | GGCCTTGGCT | TTTCTAGCCT | ATTTACCTGC | | |
| 1141 | AGGCTGAGCC | ACTCTCTTCC | CTTTCCCCAG | CATCACTCCC | CAAGGAAGAG | CCAATGTTTT | | |
| 1201 | GGACCCATAA | TCCTTTCTGC | CGACCCCTAG | TTCCCTCTGC | TCAGCCAAGC | TTGTTATCAG | | |
| 1261 | CTTTCAGGGC | CATGGTTCAC | ATTAGAATAA | AAGGTAGTAA | TTAG | | | |
| | | | | | • polyA_site | | | |

FIG. 5

METHOD OF INHIBITING BINDING OR ACTIVITY OF MIF BY ADMINISTERING A MIF ANTAGONIST

This application is a Continuation of U.S. application Ser. No. 12/781,546 filed May 17, 2010 (now issued as U.S. Pat. No. 8,617,822), which is a Divisional of U.S. application Ser. No. 11/931,442 filed Oct. 31, 2007 (now issued as U.S. Pat. No. 7,741,057), which is a Continuation of U.S. application Ser. No. 10/108,383 filed Mar. 29, 2002, now abandoned, which claims priority from U.S. Provisional Application Ser. No. 60/279,435 filed Mar. 29, 2001. The entireties of these applications are incorporated herein by reference.

BACKGROUND OF THE INVENTION

1. Field of the Invention

The present invention relates to methods and compositions for using the MHC class II invariant chain polypeptide, Ii (also known as CD74), as a receptor for macrophage migration inhibitory factor (MIF), including methods and compositions for using this receptor, as well as agonists and antagonists of MIF which bind to this receptor or which otherwise modulate the interaction of MIF with CD74 or the consequeces of such interaction, in methods for treatment of conditions characterized by locally or systemically altered MIF levels, particularly inflammatory conditions and cancer.

2. Background of the Technology

Macrophage migration inhibitory factor (MIF), the first cytokine activity to be described, has emerged to be seen as a critical regulator of the innate and adaptive immune response[1-3]. MIF is encoded by a unique gene, and crystallization studies have shown MIF to define a new protein fold and structural superfamily[4]. Despite the fact that the biological activity attributed to MIF first was described almost 30 years ago, information regarding MIF's precise role in cell physiology and immunity has emerged only recently[1-9,18]. MIF is centrally involved in macrophage and T cell activation and in the development of septic shock, arthritis, and other inflammatory conditions[2]. Also, MIF has been linked to cancer[32].

MIF is critically involved in the expression of innate and acquired immunity. MIF is released by a variety of cell types and is a necessary factor for the activation or proliferative responses of macrophages[18], T cells[6], and fibroblasts[7]. MIF's mitogenic effects proceed via an autocrine/paracrine activation pathway involving the p44/p42 (ERK-1/2) mitogen-activated protein kinase cascade[7]. MIF –/– mice are highly resistant to endotoxic shock[3], and immunoneutralization of MIF confers protection against septic shock[25] and a variety of immuno-inflammatory pathologies such as delayed-type hypersensitivity[26], arthritis[27], and glomerulonephritis[28]. MIF's actions on cells also show a number of unique features. These include a global, counter-regulatory action on glucocorticoid-induced immunosuppression[5,6], the induction of a sustained pattern of ERK-1/2 activation[7], and functional antagonism of p53-dependent apoptosis[6].

MIF's pro-inflammatory properties have been linked to its capacity to counter-regulate the immunosuppressive effects of glucocorticoids[5,6], and its interactions with cells have been presumed to require a receptor-based mechanism of action[7,8] or to reflect a specialized, intracellular mode of action[9]. Numerous in vitro and in vivo studies have been consistent with MIF acting by engagement of a cell surface receptor, however lack of progress toward the identification of candidate receptors has prompted interest in either specialized, intracellular modes of action or the potential biological role of MIF's tautomerase activity[2,21]. There also is evidence that MIF may function as an isomerase[4].

The MHC class II-associated invariant chain, Ii (CD74)[10], has been established to play an important role in the processing and transport of MHC class II proteins from the endoplasmic reticulum to the Golgi[10]. Most Ii dissociates from the class II complex as antigenic peptides load onto their class II binding sites. Approximately 2-5% of total cellular Ii also is expressed on the cell surface[17], where it has been shown to function as an accessory molecule for T cell activation[11]. Ii has been previously implicated in signaling and accessory functions for immune cell activation[11-13].

U.S. Pat. No. 5,559,028 to Humphreys, et al. discloses gene constructs for expression of wild type and mutant Ii chains in recombinant cells. U.S. Pat. No. 5,726,020 to Humphreys, et al. discloses and claims expressible reverse gene constructs and oligonucleotides that hybridize with an Ii mRNA molecule, thereby inhibiting translation of the Ii mRNA molecule.

SUMMARY OF THE INVENTION

The invention is based in part upon the identification, utilizing expression cloning and functional analyses, that the Class II-associated invariant chain polypeptide, Ii (or CD74)[10], is a cellular receptor for MIF. Thus, MIF binds to the extracellular domain of Ii, a Type II membrane protein, and Ii is required for MIF-induced cell activation and/or phenotypic changes including, for instance, signaling via the extracellular signal-related kinase (ERK)-1/2MAP kinase cascade and cell proliferation. The inventive relationship provides a mechanism for MIPs activity as a cytokine and identify it as a natural ligand for Ii, which has been previously implicated in signaling and accessory functions for immune cell activation.

Accordingly, one aspect of the present invention relates to methods for screening compounds to identify positive or negative modulators of MIF binding to, or activity in connection with binding to, CD74. In a first instance, such a method comprises a biochemical (i.e., acellular) binding assay, comprising: contacting an MHC class II invariant chain (Ii) polypeptide with MIF in the presence and absence of a test compound, and comparing the binding interaction of the MIF and Ii polypeptides in the presence of the test compound with their interaction in the absence of the test compound, whereby a compound that positively modulates the interaction of MIF with the Ii polypeptide is identified as an enhancer of MIF binding activity and a compound that negatively modulates the interaction of MIF with the Ii polypeptide is identified as an inhibitor of MIF binding activity. Enhancers so identified are candidate therapeutic agonists or enhancers of MIF, whereas inhibitors so identified are candidate therapeutic antagonists of MIF. For instance, a test compound may reinforce the binding of MIF to the Ii polypeptide (i.e., increase the affinity of the interaction) and thereby enhance the interaction of MIF and the Ii polypeptide. Such an enhancer is thereby identified as an agonist or enhancer of MIF, and is identified as a candidate therapeutic agent to enhance, independently or in connection with endogenous or exogenous MIF, MIF effects in subjects requiring such augmentation. Alternatively, a test compound that competes with MIF for binding to the Ii polypeptide or otherwise inhibits the interaction of the MIF with the Ii polypeptide is identified as an antagonist of MIF, and is identified as a candidate therapeutic agent to antagonize MIF effects in subjects requiring such antagonism. In this biochemical binding assay, the Ii polypeptide comprises the complete Ii sequence or an MIF-binding fragment thereof, and the assay is conveniently conducted with recombinantly prepared MIF and Ii peptides, one of which is optionally immobilized to a solid support, and one of which (or a binding partner thereto, such as an antibody) is labeled to facilitate detection and measurement of the MIF:Ii binding interaction.

In a second aspect, the binding assay may be a cellular binding assay, comprising CD74 expressed (either normally or as a consequence of genetic engineering for Ii expression) by a cell (prokaryotic or eukaryotic), typically on the cell surface, and MIF binding thereto is detected and measured in the presence or absence of a test compound. As in the above described biochemical or acellular assay, a comparison is made of the binding interaction of the MIF and the cell-displayed Ii polypeptide in the presence of the test compound with their interaction in the absence of the test compound, whereby a compound that positively modulates the interaction of MIF with the Ii polypeptide (i.e., increases their affinity) is identified as an enhancer of MIF binding activity and a compound that negatively modulates the interaction of MIF with the Ii polypeptide (i.e., decreases their affinity) is identified as an inhibitor of MIF binding activity. Enhancers so identified are candidate therapeutic agonists or enhancers of MIF, whereas inhibitors so identified are candidate therapeutic antagonists of MIF.

In a third aspect, the cellular assay is a signaling assay, in which the activity of an intracellular signaling cascade is measured before and after MIF is contacted to cell-displayed CD74 polypeptide, either in the presence or the absence of a test compound. Preferably, the signaling assay is an ERK-1/2 activation assay. A test compound that positively modulates the signaling activity of MIF via interaction with the Ii polypeptide is identified as an enhancer of MIF signaling activity and a compound that negatively modulates the signaling of MIF via interaction of MIF with the Ii polypeptide is identified as an inhibitor of MIF signaling activity. Enhancers so identified are candidate therapeutic agonists or enhancers of MIF, whereas inhibitors so identified are candidate therapeutic antagonists of MIF.

In a fourth aspect, the cellular assay is a cellular activity or cell phenotype assay, in which the activity or phenotype of a target cell is measured before and after MIF is contacted to cell-displayed CD74 polypeptide, either in the presence or the absence of a test compound. Preferably, the activity or phenotype assay is a proliferation assay or an assay for functional antagonism of p53-dependent apoptosis. A test compound that positively modulates the chosen cellular activity or phenotypic change mediated by MIF via interaction with the Ii polypeptide is identified as an enhancer of MIF cellular activity and a compound that negatively modulates the chosen cellular activity or phenotypic change mediated by MIF via interaction with the Ii polypeptide is identified as an inhibitor of MIF cellular activity. Enhancers so identified are candidate therapeutic agonists or enhancers of MIF, whereas inhibitors so identified are candidate therapeutic antagonists of MIF.

The invention also provides an enhancer of MIF, including an agonist, or an inhibitor, including an antagonist of MIF, identified by any of the methods above. One form of such an agonist or antagonist would be an antibody or antigen-binding fragment thereof, such as an anti-CD74 antibody. Anti-CD74 antibodies and CD74-binding fragments thereof are known in the art. For instance, the anti-CD74 antibody may be a monoclonal antibody and also may be a human, humanized or chimeric antibody, made by any conventional method.

Another aspect of the invention relates to a method of inhibiting an effect of MIF on a cell comprising on its surface an MHC class II invariant chain (Ii) polypeptide which binds MIF and thereby mediates the effect of MIF. This method comprises: contacting the cell with an antagonist or other inhibitor of MIF, where the antagonist or inhibitor inhibits, in a first instance, binding of MIF to the Ii polypeptide; in a second instance, signaling initiated by MIF:Ii interaction; and in a third instance, a change in cellular activity, metabolism or phenotype effected by MIF:Ii interaction. In any of these methods the antagonist or inhibitor may be an antibody or fragment thereof which binds to the Ii polypeptide. Alternatively, the inhibitor may be soluble Ii polypeptide or a soluble MIF-binding fragment thereof which inhibits the interaction of MIF and Ii polypeptide (or the cellular consequences of such interaction) by binding to MIF or by interacting with Ii polypeptide on the surface of a cell. In some cases, the cell comprising Ii polypeptide is present in a mammal and the antagonist or other inhibitor is administered to the mammal in a pharmaceutical composition. A mammal that would benefit from this method is a mammal suffering from a condition or disorder characterized by MIF levels locally or systemically elevated above the normal range found in mammals not suffering from such a condition. In such a case, the antagonist or inhibitor is administered in an amount effective to treat the condition or disorder. For instance, the mammal may be suffering from cancer or an inflammatory disorder, and the antagonist or inhibitor is administered in an amount effective to treat the cancer or inflammatory disorder. The inflammatory disorder may be, for instance, septic shock or arthritis.

More particularly, one aspect of the invention is a method of inhibiting an activity of MIF, which method comprises: contacting MIF with an MHC class II invariant chain (Ii) polypeptide or a fragment thereof which binds to MIF. The fragment of the MHC class II invariant chain (Ii) polypeptide which binds to MIF may be a soluble form of the polypeptide, particularly a soluble form that comprises the extracellular binding domain of this type II transmembrane polypeptide. In some cases, the MIF to be inhibited is in a mammal and the Ii polypeptide or a fragment thereof is administered to the mammal in a pharmaceutical composition. Where the mammal suffers from cancer or an inflammatory disorder, such as septic shock or arthritis, the Ii polypeptide or fragment thereof is administered in an amount effective to treat the disorder. In a further instance, the MIF antagonist or inhibitor is administered in an amount effective to treat an infectious disease, in which disease MIF or a polypeptide evolutionarily related to MIF (as evidenced by sequence homology) deriving from the infecting pathogen (whether a virus, bacterial, fungus, or especially, a parasite) is present locally, systemically, or at the host:pathogen interface.

Yet another aspect of the invention relates to a method of purifying MIF comprising: contacting a sample comprising MIF with an MHC class II invariant chain (Ii) polypeptide or a fragment thereof which binds to MIF, under conditions that promote the specific binding of MIF to the Ii polypeptide or fragment thereof, and separating the MIF:Ii polypeptide complex thereby formed from materials which do not bind to the Ii polypeptide or fragment thereof. In this method, the Ii polypeptide may be immobilized on a solid support matrix. The invention also provides a method of assaying for the presence of MIF comprising: contacting a sample with an MHC class II invariant chain (Ii) polypeptide or a fragment thereof which binds to MIF under conditions that promote the specific binding of MIF to the Ii polypeptide or fragment thereof, and detecting any MIF:Ii polypeptide or MIF:Ii polypeptide fragment complex thereby formed.

Still another method provided by the invention is a method for reducing an effect of MIF on a cell comprising on its surface an MHC class II invariant chain (Ii) polypeptide or fragment thereof which binds MIF and thereby mediates the effect of MIF. This method comprises: providing to the cell an antisense nucleic acid molecule in an amount effective to reduce the amount of Ii polypeptide produced by the cell. The antisense nucleic acid molecule specifically binds to a portion of mRNA expressed from a gene encoding the MHC class II invariant chain (Ii) polypeptide and thereby decreases translation of the mRNA in the cell and, ultimately, the level of Ii polypeptide on the surface of the cell. In this method the cell comprising the Ii polypeptide may be in a mammal, for instance, a mammal suffering from a condition or disorder characterized by MIF levels locally or systemically elevated above the normal range in mammals not suffering from such a condition or disorder. For instance, the mammal may be suffering from a cancer or an inflammatory disorder, such as septic shock or arthritis. In such a case, the antisense nucleic acid is administered in a pharmaceutical composition, in an amount effective to treat the condition or disorder.

BRIEF DESCRIPTION OF THE FIGURES

FIG. 1 illustrates high affinity binding of MIF to THP-1 monocytes. a, Alexa-MIF shows full retention of dose-dependent MIF biological activity as assessed by activation of the p44/p42 (ERK-1/2) MAP kinase cascade, visualized by western blotting of cell lysates using antibodies specific for phospho-p44/p42 or total p44/p42; and b, suppression of p53-dependent apoptosis induced by serum starvatuin (CM: complete medium, SFM: serum-free medium). MIF or Alexa-MIF were added at 50 ng/ml. Data shown are Mean±SD of triplicate wells and are representative of 3 independent experiments. Further evidence for the retention of native structure by Alexa-conjugation was provided by the measurement of MIF tautomerase activity using L-dopachrome methyl ester as substrate[25]. No difference in the tautomerase activity of Alexa-MIF versus unconjugated MIF was observed (Alexa-MIF: $\Delta OD_{475}$=0.275 sec$^{-1}$ µg$^{-1}$ protein, versus rMIF: $\Delta OD_{475}$=0.290 sec$^{-1}$ µg$^{-1}$; P=NS) c, Flow cytometric analysis shows the binding of Alexa-MIF to THP-1 monocytes is markedly enhanced by IFN-δ treatment. Competition for Alexa-MIF binding was performed in the presence of 1 µg/ml unlabeled, rMIF d, Direct visualization of Alexa-MIF binding to THP-1 monocytes by confocal microscopy THP-1 cells were grown on cover slips, incubated with INFγ (1 ng/ml) for 72 hrs and stained with Alexa-MIF (left panel) or Alexa-MIF plus excess, unlabeled rMIF (right panel). Cell bound Alexa-MIF was rapidly internalized upon shifting cells from 4° to 37° for 15 mins (right panel). Magnification: 630×e, Binding characteristics of Alexa-MIF to IFNγ-activated, THP-1 monocytes. The inset shows the binding data transformed by Scatchard analysis, indicating two distinct binding activities; one with $K_d$=3.7×10$^{-8}$ m the other with $K_d$=3.5×10$^5$, data are representative of 3 independent experiments.

FIG. 2 show that Ii is a cell surface binding protein for MIF a, Sequential cycles of fluorescence-activated cell-sorting of COS-7 cell transfectants shows enrichment for MIF binding activity b, Diagrams indicating structure of Ii (35 kDa isoform), and three of ten representative cDNA clones with MIF binding activity. IC, TM, and EC are the intracellular, transmembrane, and extracellular domains. M1 and M17 refer to two sites of alternative translation initiation. c, Flow cytometry analysis of MIF binding to Ii-expressing cells. Enhanced binding of Alexa-MIF to Ii-transfected versus control vector-transfected COS-7 cells (left panel), inhibited binding of Alexa-MIF to Ii-transfected COS-7 cells incubated with anti-Ii mAb (clone LN2) versus an isotypic mAb control (con mAb) (middle panel), and enhanced binding of Alexa-MIF to IFNγ-stimulated, THP-1 monocytes incubated with anti-Ii mAb (clone LN2) versus an isotypic mAb control (right panel). The data shown are representative of at least three independent experiments. The anti-Ii mAb, LN2 (PharMingen), is reactive with an epitope residing within 60 amino acids of the extracytoplasmic, C-terminus of the protein d, MIF binds to the extracellular domain of Ii in vitro. [$^{35}$S]-Ii protein was prepared in a coupled transcription and translation reaction utilizing plasmids encoding Ii fragments of different lengths. Protein-protein interaction was assessed by measuring bound radioactivity in 96-well plates that were pre-coated with MIF (n=6 wells per experiment). The data shown are representative of three experiments, showing that MIF binding is severely compromised with vectors expressing Ii fragments of amino acids 1-72 or 1-109 versus robust binding with vectors expressing Ii fragments of amino acids 1-149 or 1-232 (full-length).

FIG. 3 illustrates Ii mediation of MIF stimulation of ERK-1/2 (p44/p42) phosphorylation in COS-7 cells a, ERK-1/2 phosphorylation is induced by MIF in COS-7 cells transfected with Ii vector (COS-7/Ii) or control vector (COS-7/V). Cells were treated without or with various doses of rMIF for 2.5 hrs and analyzed for phospho-p44/p42 and total p44/p42 by western blotting b, There is dose-dependent inhibition of MIF-induced ERK-1/2 phosphorylation by anti-Ii mAb. COS-7 cells were transfected with an Ii vector and stimulated with 50 ng/ml MIF for 2.5 hrs in the presence of an isotypic control mAb or an anti-Ii mAb (clone LN2) at different doses. In control experiments, anti-Ii showed no effect on ERK-1/2 phosphorylation in the absence of added MIF (data not shown).

FIG. 4 illustrates western blots of MIF-induced phosphorylation a, MIF dose dependently stimulates ERK-1/2 (p44/p42) phosphorylation in human Raji B cells, as visualized by western blotting for phospho-p44/p42 b, There is inhibition of MIF-induced ERK-1/2 phosphorylation in Raji cells by anti-Ii mAb also. Raji cells were stimulated with 50 ng/ml of MIF for 2.5 hrs in the presence of an isotype control antibody (ConAb) or the two anti-Ii mAbs, —B741 or LN$^2$, each added at 50 µg/ml. c, Anti-Ii inhibits MIF-induced Raji cell proliferation quantified by $^3$H-thymidine incorporation d, Anti-Ii inhibits MIF-induced proliferation of human fibroblasts also. Antibodies were added to a final concentration of 50 µg/ml. The results shown are the Mean±SD of triplicate assays and are representative of at least three separate experiments. Anti-Ii antibodies showed no effect on cell proliferation in the absence of added MIF (data not shown).

DETAILED DESCRIPTION

The following abbreviations are used herein: Alexa-MIF: Alexa 488-MIF conjugate, ERK: extracellular-signal-regulated kinase, MHC class II-associated invariant chain (CD74), INFγ: interferon-γ, mAb: monoclonal antibody, MIF: macrophage migration inhibitory factor.

Figure 1A:
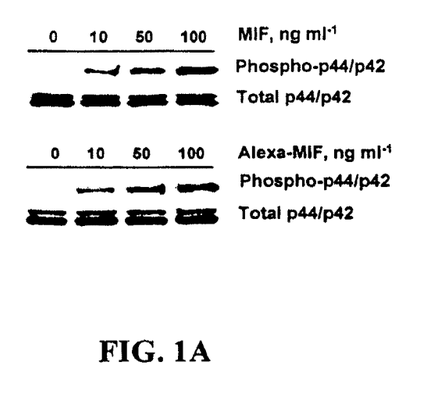
Figure 1B:
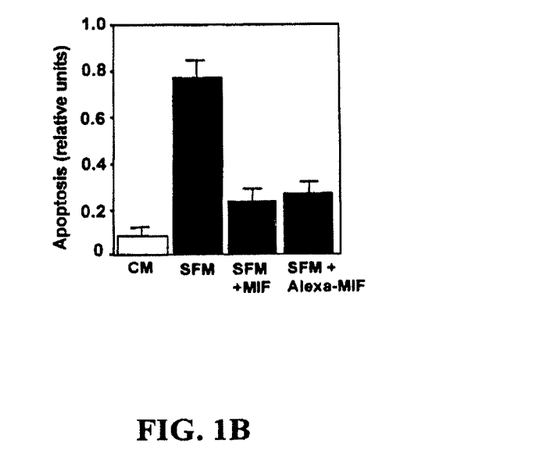
Figure 1C:
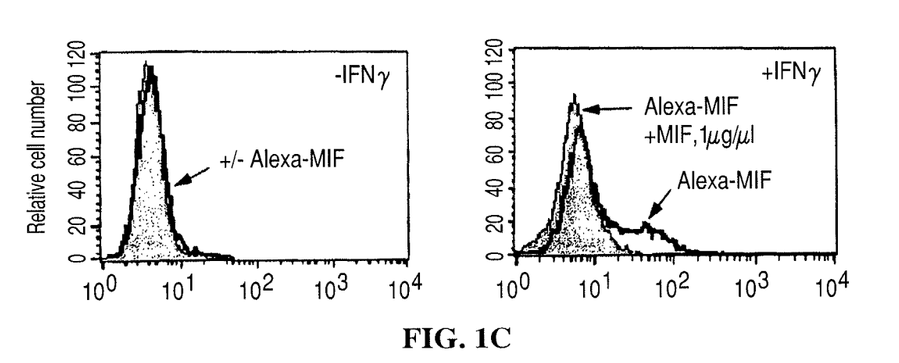
Figure 1D:
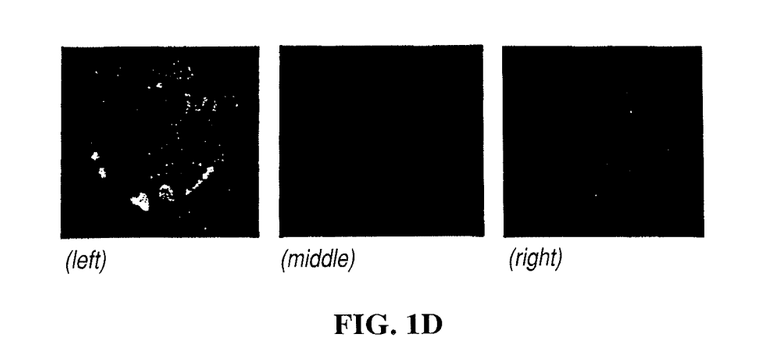
Figure 1E:
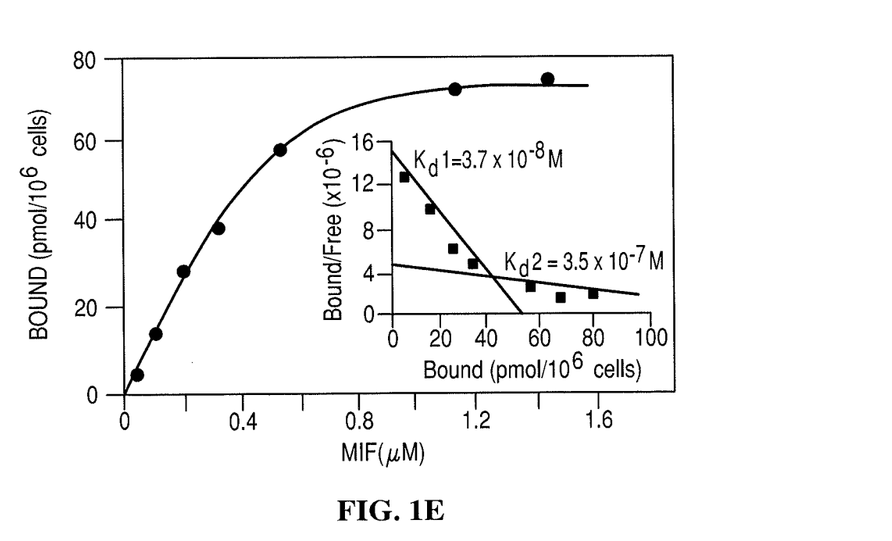

Utilizing expression cloning and functional analyses, we have identified as a cellular receptor for MIF the Class II-associated invariant chain, Ii (CD74)[10]. MIF binds to the extracellular domain of Ii, a Type II membrane protein, and Ii is required for MIF-induced cellular effects, including for instance, activation of the ERK-1/2 MAP kinase cascade and cell proliferation. These data provide a mechanism for MIF's activity as cytokine and identify it as a natural ligand for Ii, which has been previously implicated in signaling and accessory functions for immune cell activation[11-13]. We linked the fluorescent dye Alexa 488[14] to recombinant MIF by standard techniques, verified the retention of biological activity of the conjugate (FIGS. 1A,B), and conducted binding experiments with a panel of cell types known to respond to MIF. By way of illustration, using flow cytometry, we observed high-affinity binding of Alexa-MIF to the surface of the human monocytic cell line, THP-1. This binding activity was induced by activation of monocytes with interferon-γ (IFNγ), and was competed by the addition of excess, unlabeled MIF (FIG. 1C). Confocal microscopy and direct visualization of IFNγ-treated monocytes at 4° C. showed surface binding of Alexa-MIF, and cell-bound Alexa-MIF was internalized upon shifting temperature to 37° C. (FIG. 1D). Quantitative binding studies performed with increasing concentrations of Alexa-MIF revealed two apparent classes of cell surface receptors (FIG. 1E). The higher affinity binding activity showed a $K_d$ of $3.7 \times 10^4$ M and $3.1 \times 10^4$ binding sites per cell, and the lower affinity binding showed a $K_d$ of $3.5 \times 10^{-7}$ M and $4.9 \times 10^4$ sites per cell.

Figure 2A:
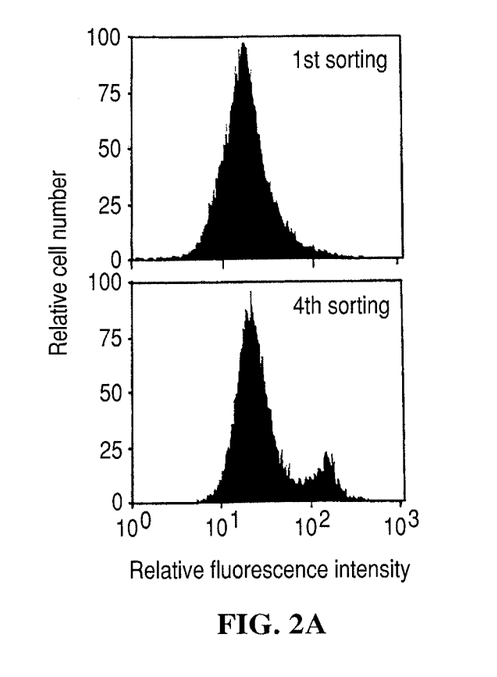
Figure 2B:
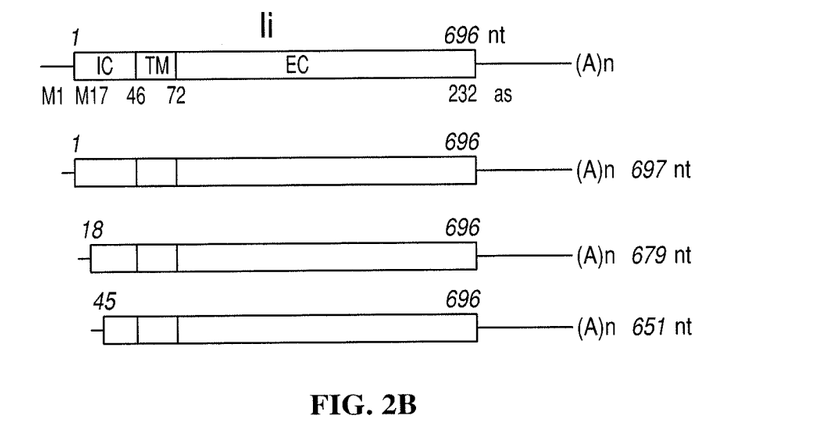

To identify the MIF receptor, we prepared cDNA from IFNγ-activated THP-1 monocytes and constructed a mammalian expression library in the lambdaZAP-CMV vector[15]. Library aliquots representing a total of $1.5 \times 10^7$ recombinants were transfected into COS-7 cells, which we had established previously to exhibit little detectable binding activity for MIF, and the transfectants were analyzed by flow cytometry for Alexa-MIF binding. Positively-staining cells were isolated by cell sorting, and the cDNA clones collected, amplified, and re-transfected into COS-7 cells for additional rounds of cell sorting (FIG. 2A). After four rounds of selection, single colonies were prepared in *E. coli* and 250 colonies were randomly picked for analysis. We sequenced 50 clones bearing cDNA inserts of ≥1.6 kB and observed that 10 encoded the Class II-associated invariant chain, Ii (CD74), a 31-41 kD Type II transmembrane protein[16]. While the isolated clones differed with respect to their total length, each was in the sense orientation and encoded a complete extracellular and transmembrane domain (FIG. 2B).

Figure 2C:
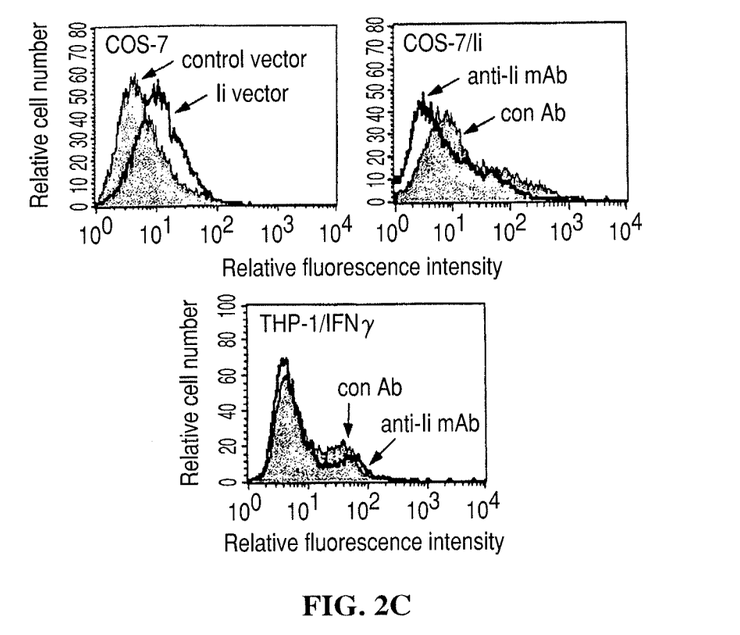
Figure 2D:
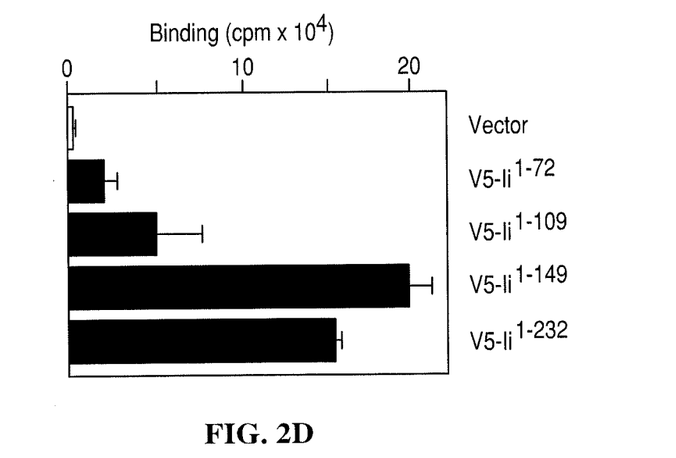

To confirm that Ii is a cell surface binding protein for MIF, we analyzed the binding of Alexa-MIF to COS-7 cells transfected with an Ii expression plasmid (FIG. 2C). Binding was inhibited by excess, unlabeled MIF (data not shown), and by an anti-Ii mAb directed against the extracellular portion of the protein. Anti-Ii mAb also inhibited the binding of Alexa-MIF to IFN-γ stimulated THP-1 monocytes. The inhibition by anti-Ii mAb of Alexa-MIF binding to THP-1 monocytes was significant, but partial, consistent with the interpretation that Ii represents one of the two classes of cell surface receptors for MIF revealed by Scatchard analysis (FIG. 1E). [$^{35}$S]-Ii protein prepared by a coupled transcription and translation reticulocyte lysate system bound to MIF in vitro, and the principal binding epitope was localized to a 40 amino acid region contained within the Ii extracellular domain (FIG. 2D).

Figure 3A:
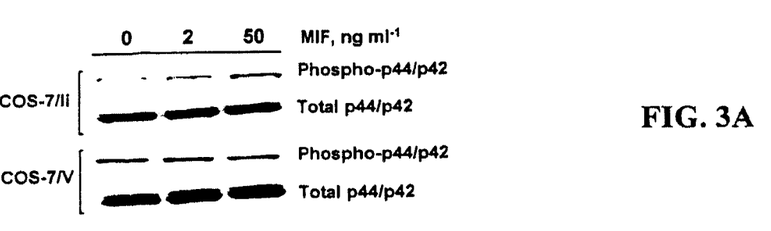
Figure 3B:
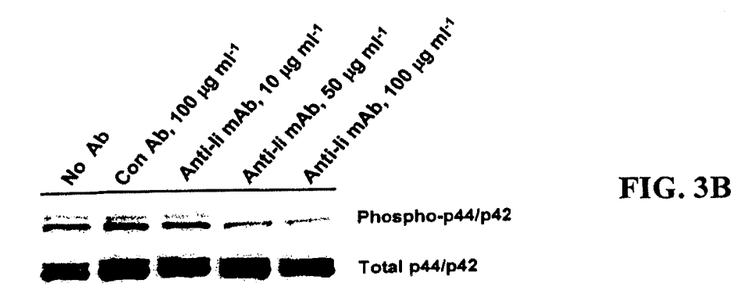
Figure 4A:
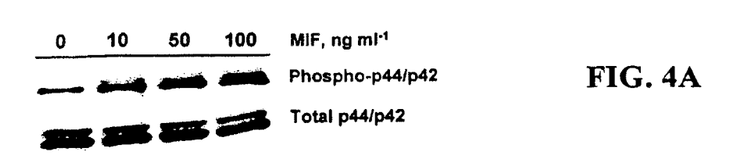
Figure 4B:
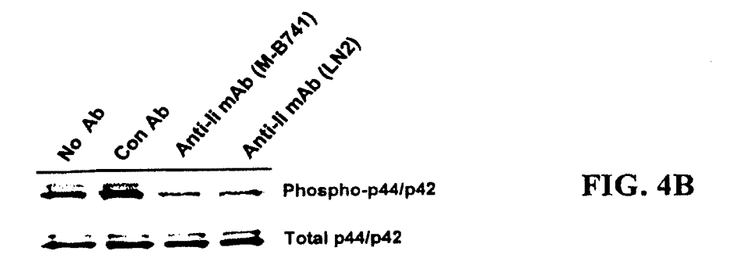
Figure 4C:
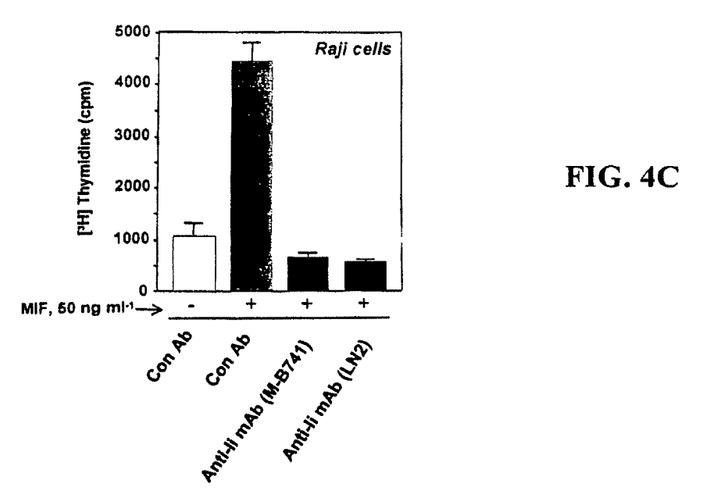
Figure 4D:
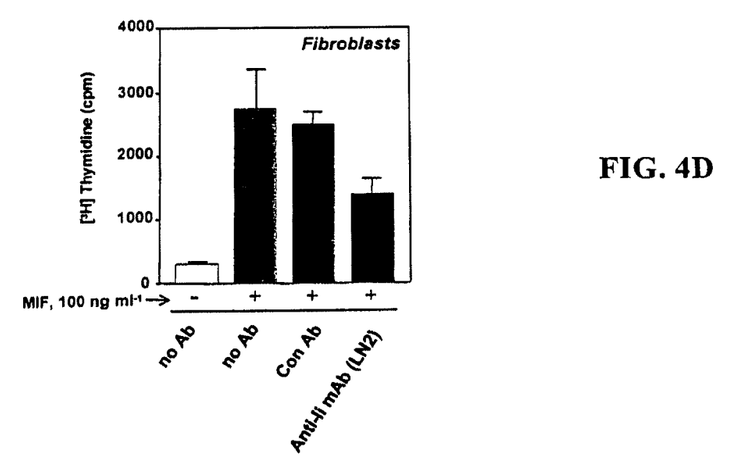
Figure 5:
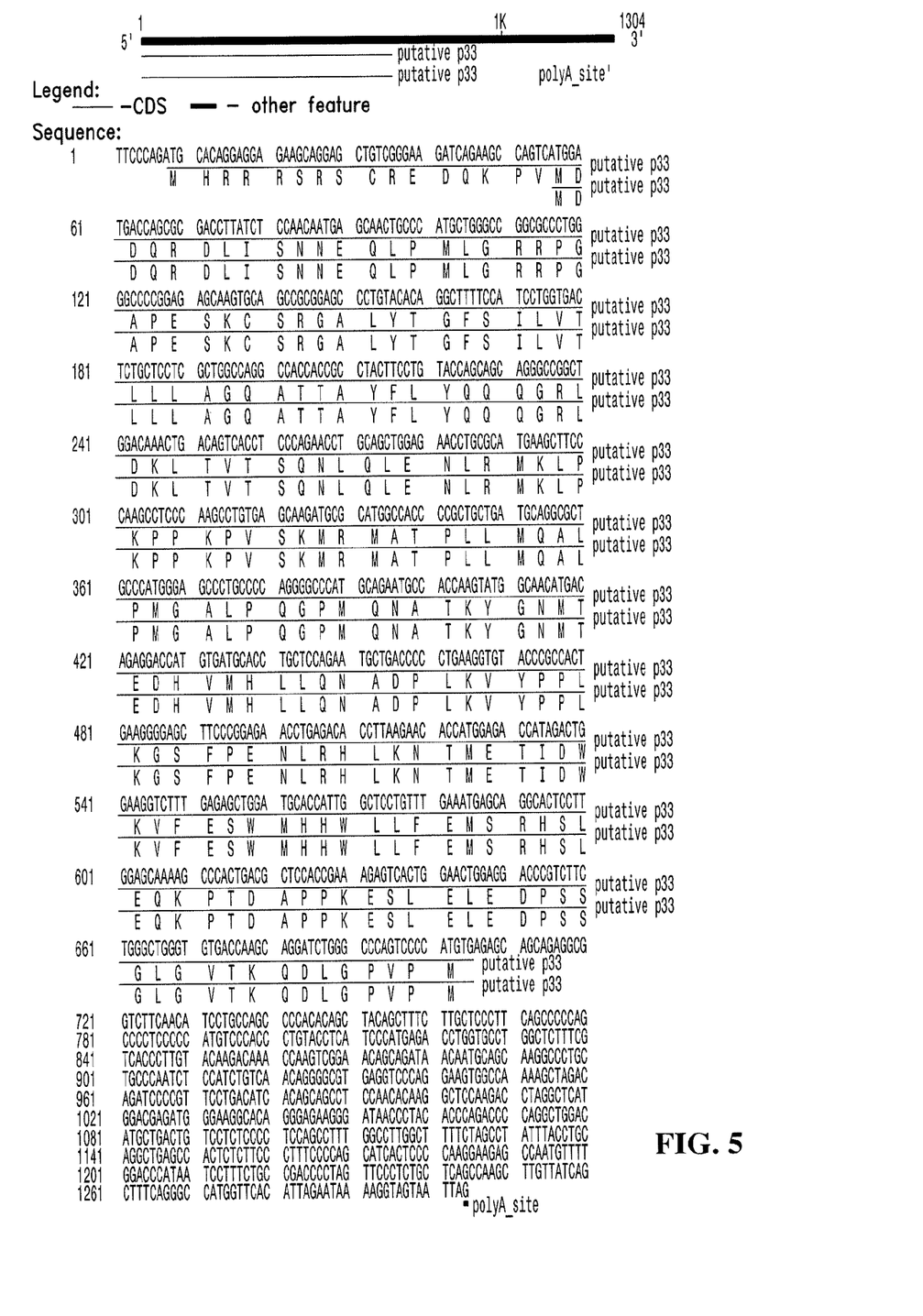
FIG. 5 shows the complete nucleotide sequence (SEQ ID NO: 1) and longest translated amino acid sequence (beginning at nt 8; SEQ ID NO:2) of the human mRNA for the Ii polypeptide (HLA-DR antigens associated invariant chain p33 [GenBank Accession Nr. X00497 M14765]), as reported in Strubin, M. et al., The complete sequence of the mRNA for the HLA-DR-associated invariant chain reveals a polypeptide with an unusual transmembrane polarity. EMBO J., 3, 869-872 (1984).

To verify the functional significance of MIF binding to Ii in an exemplary system, we examined the activity of MIF to stimulate ERK-1/2 activation and cellular proliferation in different Ii-expressing cells. We observed an MIF-mediated increase, and a dose-dependent, anti-Ii mAb-mediated decrease, in ERK-1/2 phosphorylation in Ii-transfected COS-7 cells (FIG. 3). Irrespective of Ii gene transfection however, we could not detect any proliferative effect of MIF on this monkey epithelial cell line (data not shown). We then examined the activity of MIF to induce ERK-1/2 activation and downstream proliferative responses in the human Raji B cell line, which expresses a high level of Ii[19]. MIF stimulated the phosphorylation of ERK-1/2 in quiescent Raji cells, and each of two anti-Ii mAbs blocked this stimulatory effect of MIF (FIGS. 4A,B). Of note, the inhibitory effect of anti-Ii on ERK-1/2 phosphorylation was associated with a significant decrease in the MIF-stimulated proliferation of these cells (FIG. 4C). Additionally, we confirmed the role of the MIF-Ii stimulation pathway in cells outside the immune system. MIF extends the lifespan of primary murine fibroblasts[8], and both MIF's mitogenic effects and its induction of the ERK-1/2 signal transduction cascade have been best characterized in this cell type[7]. Fibroblasts express low levels of Ii[20], and we observed that anti-Ii significantly inhibited both ERK-1/2 phosphorylation and the mitogenic effect of MIF on cultured fibroblasts (FIG. 4D and data not shown).

In prior experiments, we have experienced considerable difficulty in preparing a bioactive, $^{125}$I-radiolabelled MIF, and have observed the protein to be unstable to the pH conditions employed for biotin conjugation. By contrast, modification of MIF by Alexa 488 at a low molar density produced a fully bioactive protein which enabled identification of MIF receptors on human monocytes, and the expression cloning of Ii as a cell surface MIF receptor. These data significantly expand our understanding of Ii outside of its role in the transport of class II proteins, and support recent studies which have described an accessory signaling function for Ii in B and T cell physiology[10-13].

These findings provide a first insight into the long sought-after MIF receptor, although additional proteins are likely involved in some MIF-mediated activities. For instance, like MIF, Ii is a homotrimer[23], and the Ii intracellular domain consists of 30-46 amino acids, depending on which of two in-phase initiation codons are utilized[16]. Monocyte-encoded Ii has been shown to enhance T cell proliferative responses, and this accessory function of Ii has been linked to a specific, chondroitin-sulphate-dependent interaction between Ii and CD44[11]. We have observed an inhibitory effect of anti-CD44 on ERK-1/2 phosphorylation, but not MIF binding, in Ii-expressing cells. This is consistent with the inference that MIF-bound Ii is a stimulating ligand for CD44-mediated MAP kinase activation. CD44 is a highly polymorphic Type I transmembrane glycoprotein[24], and CD44 likely mediates some of the downstream consequences of MIF binding to Ii.

Interference in the signal transduction pathways induced by MIF-Ii interaction, for instance by providing antagonists or inhibitors of MIF-Ii interaction, offers new approaches to the modulation of cellular immune and activation responses to MIF. Agents active in this regard (agonists and antagonists and other inhibitors) have predicted therapeutic utility in diseases and conditions typified by local or systemic changes in MIF levels.

The specific binding interaction between MIF and the class II invariant chain polypeptide, Ii, also makes convenient the use of labeled MIF reagents as "Trojan horse-type" vehicles by which to concentrate a desired label or toxin in cells displaying cell surface Ii. Briefly, a desired label or toxic entity is associated with an MIF ligand (for instance, by covalent attachment), and the modified MIF ligand then is presented to cells displaying cell surface-localized Ii, which class II invariant chain polypeptide binds to and causes the internalization of the modified MIF ligand, thus causing the operative cell to become specifically labeled or toxicated. The Ii-displaying cells may be exposed to the modified MIF ligand in vitro or in vivo, in which latter case Ii-displaying cells may be specifically identified or toxicated in a patient. A wide variety of diagnostic and therapeutic reagents can be advantageously conjugated to an MIF ligand (which may be biologically active, full length MIF or an Ii-binding fragment thereof, or a mutein of either of the preceding and particularly such a mutein adapted to be biologically inactive and/or to be more conveniently coupled to a labeling or toxicating entity), providing a modified MIF ligand of the invention. Typically desirable reagents coupled to an MIF ligand include: chemotherapeutic drugs such as doxorubicin, methotrexate, taxol, and the like; chelators, such as DTPA, to which detectable labels such as fluorescent molecules or cytotoxic agents such as heavy metals or radionuclides can be complexed; and toxins such as *Pseudomonas* exotoxin, and the like.

METHODS

MIF and Antibodies.

Human recombinant MIF was purified from an *E. coli* expression system as described previously[22] and conjugated to Alexa 488[14] by the manufacturer's protocol (Molecular Probes, Eugene Oreg.). The average ratio of dye ligand to MIF homotrimer was 1:3, as determined by matrix-assisted laser-desorption ionization mass spectrometry (Kompact probe/SEQ, Kratos Analytical Ltd, Manchester, UK). Anti-human Ii monoclonal antibodies (clones LN2 and M-B741) were obtained from PharMingen (San Jose Calif.).

Flow Cytometry, Scatchard Analysis, and Confocal Microscopy. THP-1 cells ($2.5\times10^5$ cells/ml) were cultured in DMEM/10% FBS with or without IFNγ (1 ng/ml, R&D Systems, Minneapolis, Minn.) for 72 hrs. After washing, $5\times10^5$ cells were resuspended in 0.1 ml of medium and incubated with 200 ng of Alexa-MIF at 4° C. for 45 mins. The cells then were washed with ice-cold PBS (pH 7.4) and subjected to flow cytometry analysis (FACSCalibur, Becton Dickinson, San Jose, Calif.). In selected experiments, THP-1 monocytes or COS-7 transfectants were incubated with Alexa-MIF together with 50 μg/ml of an anti-Ii mAb or an isotypic control mAb. For Scatchard analysis, triplicate samples of IFNγ-treated, THP-1 cells ($1\times10^6$) were incubated for 45 mins at 4° C. in PBS/1% FBS together with Alexa-MIF (0-1.5 μM, calculated as MIF trimer), washed 3× with cold PBS/1% FBS, and analyzed by flow cytometry using CellQuest Software (Becton Dickinson, San Jose, Calif.)[29]. The specific binding curve was calculated by subtracting non-specific binding (measured in the presence of excess unlabeled MIF) from total binding. Confocal fluorescence microscopy of Alexa-MIF binding to cells was performed with an LSM 510 laser scanning instrument (Carl Zeiss, Jena Germany). THP-1 cells were incubated with INFγ for 72 hrs and washed 3× with PBS/1% FBS prior to staining for 30 mins (4° C.) with 2 ng/μl of Alexa-MIF, or Alexa-MIF plus 50 ng/μl unlabeled, rMIF.

cDNA Library Construction, Expression, and Cell Sorting.

cDNA was prepared from the poly(A)$^+$ RNA of IFNγ-activated, THP-1 monocytes, cloned into the lambdaZAP-CMV vector (Stratagene, La Jolla, Calif.), and DNA aliquots (2.5 μg/ml) transfected into $15\times10^6$ COS-7 cells by the DEAE-dextran method[30]. The transfected cells were incubated with Alexa-MIF for 45 min at 4° C., washed, and the positively-staining cells isolated[31] with a Moflo cell sorter (Cytomation, Fort Collins, Colo.). In a typical run, $1.5\times10^7$ cells/ml were injected and analyzed at a flow rate of $1\times10^4$ cells/sec. Recovery was generally 90%. Plasmid DNA was extracted from sorted cells using the Easy DNA kit (Invitrogen, Carlsbad, Calif.) and transformed into *E. coli* XL-10 gold (Stratagene, La Jolla, Calif.) for further amplification. Purified plasmid DNA then was re-transfected into COS-7 cells for further rounds of sorting. After 4 rounds of cell sorting, 250 single colonies were picked at random and the insert size analyzed by PCR. Clones with inserts >1.6 Kb were individually transfected into COS-7 cells and the MIF binding activity re-analyzed by flow cytometry.

In Vitro Transcription and Translation.

Using a full-length Ii cDNA clone as template, three truncated (1-72aa, 1-109aa, 1-149aa) and one full-length (1-232 aa) Ii product were generated by PCR and subcloned into the pcDNA 3.1/V5-HisTOPO expression vector (Invitrogen). The complete nucleotide sequence of an exemplary Ii cDNA clone and the putative Ii polypeptide forms that it encodes are presented in FIG. 5. The fidelity of vector construction was confirmed by automated DNA sequencing and the constructs then used as template for coupled transcription and translation using the TNT Reticulocyte Lysate system (Promega, Madison Wis.). The binding of [$^{35}$S]-labeled Ii to immobilized MIF was assessed by a 3 hr incubation at room temperature, as recommended by the TNT protocol.

Activity Assays.

The dose-dependent phosphorylation of ERK-1/2 was measured by western blotting of cell lysates using specific antibodies directed against phospho-p44/p42 or total p44/p42 following methods described previously[7]. MIF-mediated suppression of apoptosis was assessed in serum-deprived, murine embryonic fibroblasts by immunoassay of cytoplasmic histone-associated DNA fragments (Roche Biochemicals, Indianapolis, Ind.)[8]. Proliferation studies were performed by a modification of previously published procedures[7,8]. Human Raji B cells (American Type Tissue Culture, Rockville, Md.) were cultured in RPMI/10% FBS, plated into 96 well plates (500-1000 cells/well), and rendered quiescent by overnight incubation in RPMI/0.5% serum. The cells were washed, the RPMI/0.5% serum replaced, and the MIF and antibodies added as indicated. After an additional overnight incubation, 1 μCi of [$^3$H]-thymidine was added and the cells harvested 12 hrs later. Fibroblast mitogenesis was examined in normal human lung fibroblasts (CCL210, American Type Tissue Culture) cultured in DMEM/10% FBS, resuspended in DMEM/2% serum, and seeded into 96 well plates (150 cells/well) together with rMIF and antibodies as shown. Isotype control or anti-Ii mAbs were added at a final concentration of 50 μg/ml. Proliferation was assessed on Day 5 after overnight incorporation of [$^3$H]-thymidine into DNA.

As will be apparent to a skilled worker in the field of the invention, numerous modifications and variations of the present invention are possible in light of the above teachings. It is therefore to be understood that the invention may be practiced otherwise than as specifically described herein.

REFERENCES

1. Weiser, et al., "Molecular cloning of a cDNA encoding a human macrophage migration inhibitory factor", Proc. Natl. Acad. Sci. USA, 86, 7522-7526 (1989).
2. Metz, et al., Cytokine Reference Vol. I. Ligands Review: MIF, eds. Oppenheim, et al., Academic Press, San Diego, 703-716 (2000).
3. Bozza, et al., "Targeted disruption of migration inhibitory factor gene reveals its critical role in sepsis", J. Exp. Med., 189, 341-346 (1999).
4. Swope, et al., "Macrophage migration inhibitory factor: cytokine, hormone, or enzyme?", Rev. Physiol. Biochem. Pharmacol., 139, 1-32 (1999).

5. Calandra, et al., "MIF as a glucocorticoid-induced counter-regulator of cytokine production", Nature, 377, 68-71 (1995).
6. Bacher, et al., "An essential regulatory role for macrophage migration inhibitory factor (MIF) in T cell activation", Proc. Natl. Acad. Sci. USA, 93, 7849-7854 (1996).
7. Mitchell, et al., "Sustained mitogen-activated protein kinase (MAPK) and cytoplasmic phospholipase A2 activation by macrophage migration inhibitory factor (MIF)", J. Biol. Chem., 274, 18100-18106 (1999).
8. Hudson, et al., "A proinflammatory cytokine inhibits p53 tumor suppressor activity", J. Exp. Med., 190, 1375-1382 (1999).
9. Kleemann, et al., "Intracellular action of the cytokine MIF to modulate AP-1 activity and the cell cycle through Jabl", Nature, 408, 211-216 (2000).
10. Cresswell, et al., "Assembly, transport, and function of MHC class II molecule", Annu. Rev. Immunol., 12, 259-293 (1994).
11. Naujokas, et al., "The chondroitin sulfate form of invariant chain can enhance stimulation of T cell responses through interaction with CD44", Cell, 74, 257-268 (1993).
12. Naujokas, et al., "Potent effects of low levels of MHC class II-associated invariant chain on CD4+ T cell development", Immunity, 3, 359-372 (1995).
13. Shachar, et al., "Requirement for invariant chain in B cell maturation and function", Science, 274, 106-108 (1996).
14. Panchuk-Voloshina, et al., "Alexa dyes, a series of new fluorescent dyes that yield exceptionally bright, photo-stable conjugates", J. Histochem. Cytochem., 9, 1179-1188 (1999).
15. Wang, et al., "Expression cloning and characterization of the TGF-β Type III receptor", Cell, 67, 797-805 (1991).
16. Strubin, et al., "Two forms of the Ia antigen-associated invariant chain result from alternative initiations at two in-phase AUGs", Cell, 47, 619-625 (1986).
17. Sant, et al., "Biosynthetic relationships of the chondroitin sulfate proteoglycan with Ia and invariant chain glycoproteins" J. Immunol., 135, 416-422. (1985).
18. Calandra, et al., "The macrophage is an important and previously unrecognized source of macrophage migration inhibitory factor", J. Exp. Med., 179, 1895-1902 (1994).
19. Hansen, et al., "Internalization and catabolism of radiolabelled antibodies to MHC class-II invariant chain by B-cell lymphomas", Biochem. J., 320, 293-300 (1996).
20. Koch, et al., "Differential expression of the invariant chain in mouse tumor cells: relationship to B lymphoid development", J. Immunol., 132, 12-15 (1984).
21. Bendrat, et al., "Biochemical and mutational investigations of the enzymatic activity of macrophage migration inhibitory factor (MIF)", Biochemistry, 36, 15356-15362 (1997).
22. Thurman, et al., "MIF-like activity of natural and recombinant human interferon-gamma and their neutralization by monoclonal antibody", J. Immunol., 134, 305-309 (1985).
23. Ashman, et al., "A role for the transmembrane domain in the trimerization of the MHC Class II-associated invariant chain", J. Immunol. 163, 2704-2712 (1999).
24. Lesley, et al., "CD44 and its interaction with extracellular matrix", Adv. Immunol., 54, 271-335 (1993).
25. Calandra, et al., "Protection from septic shock by neutralization of macrophage migration inhibitory factor", Nature Med., 6, 164-170, (2000).
26. Bernhagen, et al, "An essential role for macrophage migration inhibitory factor (MIF) in the tuberculin delayed-type hypersensitivity reaction", J. Exp. Med., 183, 277-282 (1996).
27. Mikulowska, et al., "Macrophage migration inhibitory factor (MIF) is involved in the pathogenesis of collagen type II-induced arthritis in mice", J. Immunol., 158, 5514-5517 (1997).
28. Lan, et al., "The pathogenic role of macrophage migration inhibitory factor (MIF) in immunologically induced kidney disease in the rat", J. Exp. Med., 185, 1455-1465 (1997).
29. Palupi, et al., "Bovine β-lactoglobulin receptors on transformed mammalian cells (hybridomas MARK-3): characterization by flow cytometry", J. Biotech., 78, 171-184 (2000).
30. D'Andrea, et al., Expression cloning of the murine erythropoietin receptor, Cell, 57, 277-285.
31. Yamasaki, et al., "Cloning and expression of the human interleukin-6 (BSF-2/IFN beta 2) receptor", Science, 241, 825-828 (1988).
32. Chesney, et al., "An essential role for macrophage migration inhibitory factor (MIF) in angiogenesis and the growth of murine lymphoma", Mol. Med., 5, 181-191 (1999).

All publications and patent applications mentioned in the specification are herein incorporated by reference to the same extent as if each individual publication or patent application had been specifically and individually indicated to be incorporated by reference. The discussion of the background to the invention herein is included to explain the context of the invention. Such explanation is not an admission that any of the material referred to was published, known, or part of the prior art or common general knowledge anywhere in the world as of the priority date of any of the aspects listed above.

While the invention has been described in connection with specific embodiments thereof, it will be understood that it is capable of further modifications and that this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method of inhibiting the binding of macrophage migration inhibitory factor (MIF) on a cell comprising on the surface an MHC class II invariant chain (Ii) polypeptide, said method comprising:

contacting said cell with an antagonist of MIF wherein said antagonist is a recombinant polypeptide comprising a MIF protein-binding fragment of the amino acid sequence of SEQ ID NO:2, and wherein said cell is present in a mammal suffering from a B cell cancer, thereby inhibiting the binding of MIF to said Ii polypeptide.

2. A method according to claim 1 wherein said antagonist is labeled with an antibody or fragment thereof.

3. A method according to claim 1 or 2, wherein said antagonist is administered to the mammal in a pharmaceutical composition.

4. A method according to claim 3, wherein said antagonist is administered in an amount effective to treat the B cell cancer.

5. A method according to claim 1, wherein said recombinant polypeptide is a soluble form.

6. A method according to claim 5, wherein said soluble form comprises amino acids 73-232 of SEQ ID NO: 2.

7. A method according to claim 5, wherein said soluble form comprises amino acids 110-149 of SEQ ID NO: 2.

8. A method according to claim 1, wherein said cell is present in a mammal suffering from a B-cell lymphoma.

* * * * *

SEQUENCE LISTING

<160> NUMBER OF SEQ ID NOS: 2

<210> SEQ ID NO 1
<211> LENGTH: 1304
<212> TYPE: DNA
<213> ORGANISM: Homo sapiens
<220> FEATURE:
<221> NAME/KEY: CDS
<222> LOCATION: (8)...(703)

<400> SEQUENCE: 1

```
ttcccag atg cac agg agg aga agc agg agc tgt cgg gaa gat cag aag        49
        Met His Arg Arg Arg Ser Arg Ser Cys Arg Glu Asp Gln Lys
        1               5                   10 cca gtc atg gat gac cag cgc gac ctt atc tcc aac aat gag caa ctg        97
Pro Val Met Asp Asp Gln Arg Asp Leu Ile Ser Asn Asn Glu Gln Leu
15                  20                  25                  30 ccc atg ctg ggc cgg cgc cct ggg gcc ccg gag agc aag tgc agc cgc       145
Pro Met Leu Gly Arg Arg Pro Gly Ala Pro Glu Ser Lys Cys Ser Arg
                35                  40                  45 gga gcc ctg tac aca ggc ttt tcc atc ctg gtg act ctg ctc ctc gct       193
Gly Ala Leu Tyr Thr Gly Phe Ser Ile Leu Val Thr Leu Leu Leu Ala
            50                  55                  60 ggc cag gcc acc acc gcc tac ttc ctg tac cag cag cag ggc cgg ctg       241
Gly Gln Ala Thr Thr Ala Tyr Phe Leu Tyr Gln Gln Gln Gly Arg Leu
65                  70                  75 gac aaa ctg aca gtc acc tcc cag aac ctg cag ctg gag aac ctg cgc       289
Asp Lys Leu Thr Val Thr Ser Gln Asn Leu Gln Leu Glu Asn Leu Arg
    80                  85                  90 atg aag ctt ccc aag cct ccc aag cct gtg agc aag atg cgc atg gcc       337
Met Lys Leu Pro Lys Pro Pro Lys Pro Val Ser Lys Met Arg Met Ala
95                  100                 105                 110 acc ccg ctg ctg atg cag gcg ctg ccc atg gga gcc ctg ccc cag ggg       385
Thr Pro Leu Leu Met Gln Ala Leu Pro Met Gly Ala Leu Pro Gln Gly
                115                 120                 125 ccc atg cag aat gcc acc aag tat ggc aac atg aca gag gac cat gtg       433
Pro Met Gln Asn Ala Thr Lys Tyr Gly Asn Met Thr Glu Asp His Val
            130                 135                 140 atg cac ctg ctc cag aat gct gac ccc ctg aag gtg tac ccg cca ctg       481
Met His Leu Leu Gln Asn Ala Asp Pro Leu Lys Val Tyr Pro Pro Leu
            145                 150                 155 aag ggg agc ttc ccg gag aac ctg aga cac ctt aag aac acc atg gag       529
Lys Gly Ser Phe Pro Glu Asn Leu Arg His Leu Lys Asn Thr Met Glu
160                 165                 170 acc ata gac tgg aag gtc ttt gag agc tgg atg cac cat tgg ctc ctg       577
Thr Ile Asp Trp Lys Val Phe Glu Ser Trp Met His His Trp Leu Leu
175                 180                 185                 190 ttt gaa atg agc agg cac tcc ttg gag caa aag ccc act gac gct cca       625
Phe Glu Met Ser Arg His Ser Leu Glu Gln Lys Pro Thr Asp Ala Pro
                195                 200                 205 ccg aaa gag tca ctg gaa ctg gag gac ccg tct tct ggg ctg ggt gtg       673
Pro Lys Glu Ser Leu Glu Leu Glu Asp Pro Ser Ser Gly Leu Gly Val
            210                 215                 220 acc aag cag gat ctg ggc cca gtc ccc atg tgagagcagc agaggcggtc         723
Thr Lys Gln Asp Leu Gly Pro Val Pro Met
225                 230 ttcaacatcc tgccagcccc acacagctac agctttcttg ctcccttcag ccccagccc      783 ctcccccatg tcccaccctg tacctcatcc catgagacct ggtgcctggc tctttcgtca     843
cccttgtaca agacaaacca agtcggaaca gcagataaca atgcagcaag ccctgctgc      903 ccaatctcca tctgtcaaca ggggcgtgag gtcccaggaa gtggccaaaa gctagacaga     963
tccccgttcc tgacatcaca gcagcctcca acacaaggct ccaagaccta ggctcatgga    1023
cgagatggga aggcacaggg agaagggata accctacacc cagaccccag gctggacatg    1083
ctgactgtcc tctcccctcc agcctttggc cttggctttt ctagcctatt tacctgcagg    1143
ctgagccact ctcttccctt tccccagcat cactccccaa ggaagagcca atgttttgga    1203
cccataatcc tttctgccga cccctagttc cctctgctca gccaagcttg ttatcagctt    1263
```

```
tcagggccat ggttcacatt agaataaaag gtagtaatta g                              1304
```

<210> SEQ ID NO 2
<211> LENGTH: 232
<212> TYPE: PRT
<213> ORGANISM: Homo sapiens

<400> SEQUENCE: 2

```
Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Pro Met
            115                 120                 125

Gln Asn Ala Thr Lys Tyr Gly Asn Met Thr Glu Asp His Val Met His
130                 135                 140

Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
                165                 170                 175

Asp Trp Lys Val Phe Glu Ser Trp Met His His Trp Leu Leu Phe Glu
            180                 185                 190

Met Ser Arg His Ser Leu Glu Gln Lys Pro Thr Asp Ala Pro Pro Lys
        195                 200                 205

Glu Ser Leu Glu Leu Glu Asp Pro Ser Ser Gly Leu Gly Val Thr Lys
    210                 215                 220

Gln Asp Leu Gly Pro Val Pro Met
225                 230
```